Figure 1:
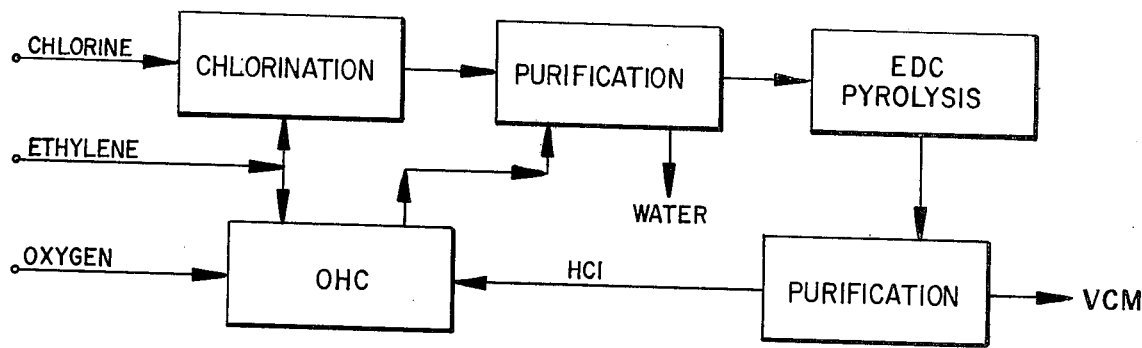
Figure 2:
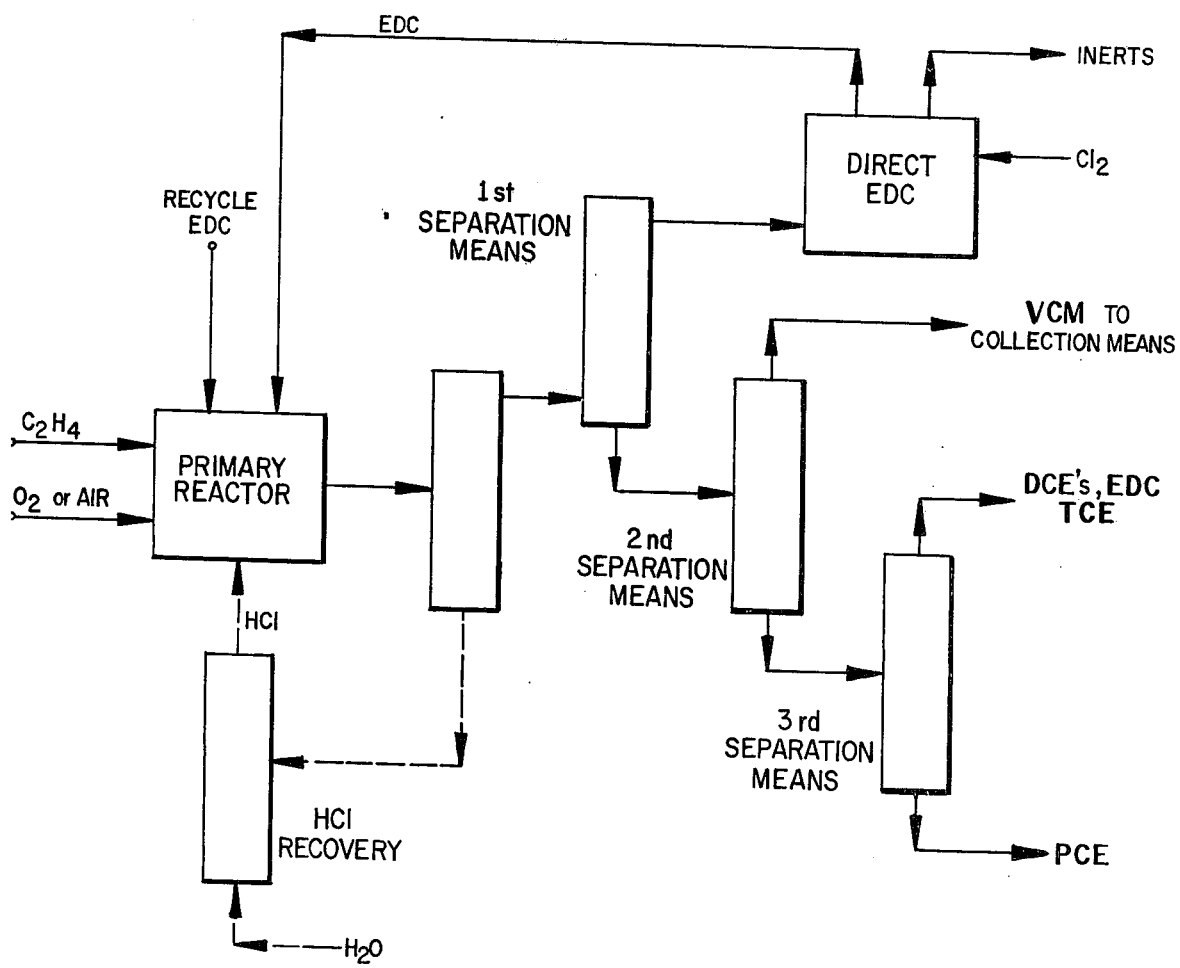

United States Patent [19]

Lemanski et al.

[11] 4,115,323

[45] Sep. 19, 1978

[54] CATALYST AND PROCESS FOR PRODUCTION OF VCM

[75] Inventors: Michael F. Lemanski, Euclid; Frederick C. Leitert, North Madison; Carl G. Vinson, Jr., Mentor, all of Ohio

[73] Assignee: Diamond Shamrock Corporation, Cleveland, Ohio

[21] Appl. No.: 843,721

[22] Filed: Oct. 19, 1977

[51] Int. Cl.$^2$ .................. B01J 23/80; B01J 23/60
[52] U.S. Cl. .................. 252/455 R; 252/459; 252/460; 252/466 PT; 252/472
[58] Field of Search .......... 252/455 R, 466 PT, 459, 252/460, 472

[56] References Cited

U.S. PATENT DOCUMENTS

| | | | |
|---|---|---|---|
| 3,641,121 | 2/1972 | Swift | 252/460 |
| 3,651,167 | 3/1972 | de Rosset | 252/466 PT |
| 3,790,504 | 2/1974 | Duhaut et al. | 252/455 R |
| 4,021,374 | 5/1977 | Petro et al. | 252/466 PT |
| 4,055,512 | 10/1977 | Kageyama et al. | 252/455 R |

*Primary Examiner*—George Grasanakis
*Attorney, Agent, or Firm*—John C. Tiernan

[57] ABSTRACT

The present invention relates to a novel catalyst for production of VCM containing a salt of rhodium or platinum, a salt of iron or copper, and a salt of zinc; impregnated on an alumina, titania, zirconia, silica, or silica alumina support.

The catalyst can be employed in a fixed or fluid bed reactor to adiabatically produce vinyl chloride from a feed stream containing ethylene, a source of chlorine, a source of elemental oxygen, and, optionally, ethylene dichloride.

7 Claims, 2 Drawing Figures

CATALYST AND PROCESS FOR PRODUCTION OF VCM

BACKGROUND OF THE INVENTION

Vinyl chloride, or monochloroethylene ($CH_2=CHCl$), has been known since the early nineteenth century. With the growth of polyvinyl chloride polymers (PVC), vinyl chloride as the basic "starting" material became more commonly referred to as vinyl chloride monomer (VCM), and has become a product of extremely important commercial significance. During 1976, almost five billion pounds of PVC were produced in the United States alone.

VCM has been commercially synthesized by various combinations of processes and procedures, but these generally fall into one of two basic routes: (1) the hydrochlorination of acetylene, or (2) the oxyhydrochlorination (OHC) and/or chlorination of ethylene to 1,2-dichloroethane (EDC), followed by a pyrolysis reaction in which the dichloroethane is pyrolyzed to VCM and hydrogen chloride. Except where the context otherwise clearly indicates, the terms chlorinating, chlorination, oxychlorination and/or oxyhydrochlorination reaction, etc., shall be understood to denote any of the various procedures for producing EDC from ethylene.

While the hydrochlorination of acetylene is obviously the easier and more direct route chemically, acetylene is a significantly higher-priced hydrocarbon than ethylene. On the other hand, the economic advantage of ethylene as a starting material is, in part, offset by the more complex series of reactions required and also by the energy imbalance which is inherent in these reactions when conducted separately.

The ethylene route involves first an exothermic chlorination reaction most frequently followed by an endothermic pyrolysis reaction. In terms of the total calories of heat produced, the heat generated by such an OHC reaction is two to three times greater than the heat input required for the pyrolysis reaction. In spite of this, it has heretofore been impossible, in commercial operation, to conduct the pyrolysis reaction employing only the heat from the OHC reaction, because the OHC reaction is usually carried out at a temperature about 200° C lower than the temperature of the pyrolysis reactor. In essence, while the quantity of heat generated may be sufficient, it is not heat of a sufficient "quality," (that is, a high enough temperature) and additional energy input has heretofore generally been required for the pyrolysis reaction.

It is obvious, of course, that the ideal solution would be a process in which heat generated in the chlorination reaction(s) would be of sufficient quality, as well as quantity, to conduct the pyrolysis reaction; such as by lowering the temperature at which the pyrolysis reaction can be conducted and/or raising the temperature of the chlorination reactor, while maintaining substantially the same efficiency in conversion of ethylene to VCM. While such a process will be referred to hereinafter as an "adiabatic process," it will be clear that it does not require heat balance, but merely the elimination of the need for any substantial independent input of higher temperature heat.

In its most desirable form, such an adiabatic process would compromise chlorination of ethylene to dichloroethane in an exothermic OHC reaction, which would provide the heat for substantially simultaneous, highly VCM selective, in situ pyrolysis of the dichloroethane to VCM and hydrogen chloride. Since the HCl by-product of the pyrolysis reaction could be consumed in situ for the OHC reaction, such a process would eliminate not only the need to collect the heat output of the chlorination reaction and the need to transfer that heat to a pyrolysis reactor, but it would also eliminate or substantially reduce the need to recover, purify and recycle most of the hydrogen chloride by-product.

A "simultaneous reaction" process is, in fact, taught in British Pat. No. 1,159,296. However, the specific catalyst used in the teaching of this British patent is not very highly selective to VCM, and the resultant overall low percentage yield of ethylene to VCM greatly reduces the potential commercial significance. In addition, this process requires that significant volumes of hydrogen chloride be fed to the reaction necessitating recovery and recycle of this raw material at considerable operating expense.

A process having a more desirable ethylene to VCM yield is taught in U.S. Pat. No. 3,291,846 (Otsuka et al.) where a gaseous mixture of ethylene, chlorine and ethylene dichloride are fed at a temperature of from 450° to 550° C to a first reactor (a fluidized bed containing only sand) to form a product containing VCM, HCl and unreacted ethylene from which the VCM is removed, leaving only hydrogen chloride and ethylene, to which oxygen is then added. The mixture of ethlyene, oxygen, and hydrogen chloride is then fed to a second reactor, where it is catalytically oxyhydrochlorinated to a mixture of ethylene dichloride and chlorinated by-products, with the ethylene dichloride being purified, particularly of oxygen, and recycled to the first reactor. In essence, this process comprises a non-catalytic vapor phase chlorination of a stoichiometric excess of ethylene, at a temperature in excess of that at which EDC would normally be pyrolyzed to VCM, and in which the reaction equilibrium is further directed towards the production of VCM by employing a feed stream in which the ratio of carbon to chlorine is greater than 2:1. As with most non-catalytic reactions to yield a reactive intermediate, this procedure can be expected to produce large quantities of by-product chlorohydrocarbons.

The detailed steps of a balanced process involve much more than simply achieving an energy balance or elimination of the need for independent heat input to the pyrolysis reaction. It should also provide a high degree of selectivity to VCM, while minimizing by-products by shifting the reaction equilibrium either away from this production or to a form in which they can be recycled to the original reactor.

For example, since the energy output of the OHC reaction is about twice the energy input required for the pyrolysis reaction, the most desirable feed to the reactor is not just an oxygen and chlorine source, plus ethylene, but an oxygen and chlorine source, plus a mixture of ethylene and EDC. This provides not only energy balance, but also materials balance in that the HCl, ethylene, oxygen, and unpyrolyzed EDC can be recycled to the original reactor either directly, or after a separate OHC reaction in which the HCl and ethylene are converted to EDC.

There are a wide variety of catalytic oxyhydrochlorination processes well known to those skilled in the art, most frequently employing cupric chloride (alone or with a modifier), impregnated on an alumina, silica, or other support. While this is, perhaps, the most widely employed catalyst for oxyhydrochlorination, other chlorides, including iron chlorides, have been employed. A wide variety of materials have been employed with the cupric chloride to modify one or more of the characteristics of the catalyst. Potassium chloride is probably the most frequently employed modifying material, usually added to reduce the evaporation losses of cupric chloride, though other alkali metal chlorides have been similarly employed.

For example, in the aforementioned British Pat. No. 1,159,296, the catalyst employed was copper chloride and potassium chloride on a diatomaceous earth support. As previously noted, the selectivity to VCM exhibited by this catalyst is low. In addition, while the catalyst was reported to be suitable for use in either fixed or fluid bed reactors, the specification indicates that only the fixed bed reactor could provide operation under adiabatic conditions.

DRAWINGS

In the drawings,

FIG. I is a diagramatic illustration of the conventional process for producing VCM by oxychlorination of ethylene to EDC, which is subsequently pyrolyzed to VCM and HCl.

FIG. II is a diagramatic illustration of one of the preferred embodiments of the process of the present invention.

SUMMARY OF THE INVENTION

The novel catalyst of the present invention comprises from about 0.01 to about 6% by weight of a salt of rhodium or platinum, from about 0.01 to about 15% of a salt of iron or copper, and from about 1.0 to about 25% of a salt of zinc; impregnated on a support selected from the group consisting of alumina, titania, zirconia, silica, and silica alumina, said percentages expressing the metal content of each component as a function of the total weight of the catalyst.

This catalyst can be employed in a fixed or fluid bed reactor to adiabatically produce vinyl chloride from a feed stream containing ethylene, a source of chlorine, and a source of elemental oxygen. The feed stream may optionally contain ethylene dichloride. In the adiabatic process of the present invention, the reactor is maintained at a pressure of from 0 to about 150 psi and a temperature of from about 325° to about 450° C for a contact time of from about 2 to about 60 seconds.

The vinyl chloride end product can be separated and recovered by any conventional means, well known to those skilled in the art. The output from the reactor, particularly a commercial reactor, will also contain a mixture of by-products along with the VCM, including unreacted ethylene, unpyrolyzed dichloroethane, air or oxygen, carbon oxides, chlorine or hydrogen chloride, and more highly chlorinated chloroethanes and chloroethylenes. The unpyrolyzed EDC, of course, can be recycled to the original reactor feed or separately pyrolyzed to VCM in a conventional pyrolysis furnace. Also, the ethylene could be oxychlorinated to EDC, or chlorinated with liquid or gaseous chlorine to produce EDC, for use as feed to the original reactor. The higher chlorinated chloroethanes and chloroethylenes can be processed further to make products of commercial significance, e.g. perchloroethylene, trichloroethylene, etc.

PREFERRED EMBODIMENTS

The preferred catalyst of the present invention comprises (based on the metal content) from about 0.03 to about 2.0% to by weight rhodium chloride, 0.02 to about 10% iron chloride, and 2.2 to about 15% zinc chloride impregnated on a suitable support or carrier. The preferred catalyst of the present invention may also contain from 0 to about 3.0% by weight lithium chloride. The preferred support of the present invention is a high purity alumina support having a surface area of from about 0.1 to about 10.0 m$^2$/g and containing from about 0.2 to about 1.0% by weight sodium oxide.

While the preferred catalyst of the present invention is defined and discussed in terms of the chlorides of rhodium, iron, zinc, and lithium, it will, of course, be obvious to those skilled in the art that other suitable salts of these metals can be employed in preparation of the catalyst, either prior to charging to the OHC reactor, and/or in situ followed by the addition of a chlorine source to the reactor.

The novel method of the present invention is a continuous process in which:

(a) feeding ethylene, a source of oxygen, and a source of chlorine to a primary reactor, which has been charged with a catalyst as defined hereinbefore;

(b) oxyhydrochlorinating said ethylene to EDC and simultaneously pyrolyzing said EDC in situ to VCM and hydrogen chloride;

(c) removing the VCM from the mixture of gaseous feed materials, end products, and by-products, then (d) removing any unreacted chlorine source, unreacted ethylene, and unpyrolyzed EDC and recycling them either directly to the feed stream to the primary reactor and/or indirectly after chlorination or oxyhydrochlorination of any unreacted ethylene to EDC, said reaction being carried out at a pressure from about 0 to about 150 psi, at a contact time from about 2 to about 60 seconds, and at a temperature from about 325° to about 450° C, said temperature being maintained substantially free of the need of any independent input of heat energy other than that which may be required for initial start-up of said continuous process and/or preheating of the reactants.

FIG. I is a diagramatic illustration of a conventional process for producing VCM in which ethylene is converted to EDC either by reaction with chlorine and/or oxychlorination with chlorine or hydrogen chloride, the exit gases being passed through a purification means to separate the EDC, which is then passed into a pyrolysis reactor in which the EDC is pyrolyzed to VCM and HCl, the exit gases from the pyrolysis reactor being passed to a second purification means in which the VCM is separated from the HCl, the VCM being collected by any of a wide variety of means well known to those skilled in the art, and the HCl being recycled to the oxychlorination reactor.

The energy balance for a typical process such as that of FIG. I would be approximately as follows:

ENERGY BALANCE (KCAL/MOLE)

A. $\frac{1}{2}$ ($C_2H_4$ + $Cl_2$ → $C_2H_4Cl_2$)  $\Delta H = -22$

B. $\frac{1}{2}$ ($C_2H_4$ + HCl + $\frac{1}{2}$ $O_2$ → $C_2H_4Cl_2$ + $H_2O$)  $\Delta H = -29$ C. 1/40 ($C_2H_4$ + 2.75 $O_2$ → 1.5 $CO_2$ + 0.5 CO + 2 $H_2O$)  $\Delta H = -6$ D. $C_2H_4Cl_2$ → $C_2H_3Cl$ + HCl  $\Delta H = +17$ In examining the foregoing, it will be noted that while such a conventional process produces 57 kilo calories per gram-mole (kcal/mole) in the exothermic reactions, and only requires a heat input of 17 kcal/mole for the pyrolysis reaction, the 17 kcal/mole must be independently supplied as high temperature heat, and the 57 kcal/mole produced can be employed, if at all, only in low priority applications, such as the production of steam and/or the purification of EDC.

FIG. II illustrates one of the preferred embodiments of the process in the present invention in which ethylene, air, HCl and EDC are fed to a primary reactor maintained at a temperature of about 350° C and a pressure of from 0 to 45 psig, in which the ethylene is oxychlorinated to EDC, which, alone and/or with the EDC in the feed stream, is simultaneously pyrolyzed to VCM. The exit gases are quenched to cool the gases and remove the HCl (for recycle to the primary reactor), the gases from the quench being fed to a first separation means at a suitable temperature wherein the ethylene is removed at the top of the separation means, as a gas, and the VCM and other chlorinated hydrocarbons are removed, as a liquid, through the bottom of the separation means and fed to a second separation means in which the VCM is volatilized from the remaining chlorinated hydrocarbons to a suitable collection means while the EDC is subsequently removed from the other chlorinated hydrocarbons in a third separation means for the recycle to the primary reactor. The unreacted ethylene from the first separation means is fed to a direct chlorination reactor, together with a suitable source of chlorine, and converted to EDC, which is then fed to the primary reactor.

The following examples will serve by way of illustration and not by way of limitation to describe the novel catalyst and process of the present invention.

EXAMPLE 1

The catalyst was prepared by impregnating alumina pellets (3/16 inch diameter, 2.6 m$^2$/g surface area) with an aqueous solution containing $FeCl_2.4H_2O$, $RhCl_3.3H_2O$, $ZnCl_2$ and LiCl. After filtration, drying and calcination at 400° C for 8 hours, the metals content of the catalyst was 1.3 wt% Fe, 0.054 wt% Rh, 3.3 wt% Zn and 0.37 wt% Li.

The catalyst was charged to a 1.25 inch OD tubular quartz reactor, heated to 350° C, and a gas mixture containing 16.7 mole % HCl, 16.7 mole % $C_2H_4$, 16.7 mole % 1,2-dichloroethane, 16.7 mole % nitrogen and 33.3 mole % air was passed through at a volumetric flow rate of 750 cc/min, operating pressure of 0 psig and a 7.5 sec contact time. Analysis of the exit gas by gas chromatographic analysis ("GC analysis") based on carbon-containing products gave the following results:

| Compound | mole % |
| --- | --- |
| $CO_x$ | 6.55 |
| $C_2H_3Cl$ | 38.86 |
| c- and t-$C_2H_2Cl_2$ | 1.30 |
| 1,2-$C_2H_4Cl_2$ | 24.92 |
| $C_2H_4$ | 28.37 |

EXAMPLE 2

Example 1 was repeated except that the operating temperature was increased to 400° C. GC analysis based on carbon-containing products gave the following:

| Compound | mole % |
| --- | --- |
| $CO_x$ | 8.81 |
| $C_2H_3Cl$ | 40.39 |
| 1,1-$C_2H_2Cl_2$ | .15 |
| c- and t-$C_2H_2Cl_2$ | 1.91 |
| 1,2-$C_2H_4Cl_2$ | 10.25 |
| $C_2HCl_3$ | .70 |
| $C_2Cl_4$ | .48 |
| $C_2H_4$ | 37.31 |

EXAMPLE 3

The same support and impregnation procedure as in Example 1 were utilized to obtain a catalyst composition containing 1.2 wt % Fe, 0.044 wt% Rh, 2.7 wt% Zn and 0.32 wt% Li. The same operating conditions were employed, except the operating pressure was 45 psig with a volumetric flow rate of 3000 cc/min. GC analysis of the carbon-containing products showed the following:

| Compound | mole % |
| --- | --- |
| $CO_x$ | 10.15 |
| $C_2H_3Cl$ | 25.97 |
| c- and t-$C_2H_2Cl_2$ | 0.84 |
| 1,2-$C_2H_4Cl_2$ | 28.12 |
| $C_2Cl_4$ | 0.31 |
| $C_2H_4$ | 34.61 |

EXAMPLE 4

The catalyst was prepared by impregnating a fluidized alimina support (physical properties similar to those in Example 1) so that the final metals concentrations were 1.5 wt% Fe, 0.074 wt% Rh, 3.4 wt% Zn and 0.4 wt% Li.

The catalyst was charged to a quartz tubular fluid bed reactor maintained at 350° C. The same molar gas ratio as in Example 1 was utilized at a volumetric flow rate of 800 cc/min, corresponding to an 8 sec contact time, at an operating pressure of 0 psig. GC analysis of the carbon-containing effluent from the reactor produced the following:

| Compound | mole % |
| --- | --- |
| $CO_x$ | 7.54 |
| $C_2H_3Cl$ | 39.60 |
| c- and t-$C_2H_2Cl_2$ | 0.98 |
| 1,2-$C_2H_4Cl_2$ | 26.76 |
| $C_2H_4$ | 25.12 |

EXAMPLE 5

Example 4 was repeated except that a volumetric flow rate of 1280 cc/min, corresponding to a 5 sec contact time was employed. The subsequent GC analysis based on carbon-containing products follows:

| Compound | mole % |
| --- | --- |
| $CO_x$ | 4.92 |
| $C_2H_3Cl$ | 28.49 |
| c- and t-$C_2H_2Cl_2$ | 0.15 |
| 1,2-$C_2H_4Cl_2$ | 36.17 |
| $C_2H_4$ | 30.27 |

EXAMPLE 6

Example 4 was repeated except that a volumetric flow rate of 640 cc/min, corresponding to a 10 sec contact time was utilized. The GC analysis was as follows:

| Compound | mole % |
|---|---|
| $CO_x$ | 7.98 |
| $C_2H_3Cl$ | 43.71 |
| c- and t-$C_2H_2Cl_2$ | .61 |
| 1,2-$C_2H_4Cl_2$ | 19.46 |
| $C_2H_4$ | 28.24 |

EXAMPLE 7

Example 4 was again repeated except that the following molar gas ratio was employed: 20 mole % $C_2H_4$, 20 mole % ethylene dichloride, 20 mole % nitrogen and 40 mole % air (no HCl). The GC analysis follows:

| Compound | mole % |
|---|---|
| $CO_x$ | 3.05 |
| $C_2H_3Cl$ | 30.83 |
| 1,2-$C_2H_4Cl_2$ | 33.27 |
| $C_2H_4$ | 32.85 |

EXAMPLE 8

An impregnation was carried out on a low surface area (1 m²/g) alumina support such that the final metals concentrations were 1.2 wt% Fe, 0.049 wt% Rh, 3.0 wt% Zn and 0.34 wt% Li. Operating conditions were the same as in Example 4 except the molar gas ratios were: 25 mole % $C_2H_4$, 25 mole % HCl, 25 mole % $N_2$ and 25 mole % air (no 1,2-dichlorethane). The GC analysis resulted in the following:

| Compound | mole % |
|---|---|
| $CO_x$ | 5.68 |
| $C_2H_3Cl$ | 16.62 |
| c- and t-$C_2H_2Cl_2$ | .50 |
| 1,2-$C_2H_4Cl_2$ | 1.25 |
| $C_2HCl_3$ | 0.11 |
| $C_2H_4$ | 75.84 |

EXAMPLE 9

The catalyst was prepared by impregnating a low surface area fluidizable alumina support with a solution containing $CuCl_2.2H_2O$, $RhCl_3.3H_2O$, $ZnCl_2$ and LiCl.

The composition of the resulting catalyst corresponded to 1.7 wt % Cu, 0.084 wt % Rh, 4.0 wt % Zn and 0.43 wt % Li. The operating conditions were identical to those employed in Example 4. GC analysis of the carbon-containing effluent gave the following:

| Compound | mole % |
|---|---|
| $CO_x$ | 7.16 |
| $C_2H_3Cl$ | 41.90 |
| c- and t- $C_2H_2Cl_2$ | .84 |
| 1,2-$C_2H_4Cl_2$ | 28.48 |
| $C_2H_3Cl_3$ | .19 |
| $C_2HCl_5$ | .18 |
| $C_2H_4$ | 21.25 |

EXAMPLE 10

A solution containing $FeCl_2.4H_2O$, $H_2PtCl_6.6H_2O$, $ZnCl_2$ and LiCl was used to impregnate a low surface area fluidizable alumina support. The composition of the resulting catalyst after calcination at 400° C corresponded to 1.8 wt % Fe, 0.17 wt % Pt, 4.0 wt % Zn and 0.56 wt % Li. The operating conditions were identical to those employed in Example 4. GC analysis of the carbon-containing effluent follows:

| Compound | mole % |
|---|---|
| $CO_x$ | 5.16 |
| $C_2H_3Cl$ | 37.72 |
| 1,1-$C_2H_2Cl_2$ | .16 |
| c- and t- $C_2H_2Cl_2$ | .92 |
| 1,2- $C_2H_4Cl_2$ | 25.14 |
| $C_2H_3Cl_3$ | .33 |
| $C_2H_4$ | 30.57 |

Further series of experiments were conducted in a similar manner. In the first of these, one or more of the catalyst components was omitted, and the data developed in this series of experiments is set forth in Table I. In the second series of experiments, the concentration of individual catalyst components was varied, yielding the data set forth in Table II.

TABLE I

Effect of Catalyst Constituents on Activity

| Run # | %Fe | %Rh | %Zn | %Li | %$CO_x$ | %VCM | %DCE's | %EDC | %Others | %$C_2H_4$ conv. | Reactor* |
|---|---|---|---|---|---|---|---|---|---|---|---|
| 1 | 0 | .059 | 2.4 | .22 | 1.9 | 33.5 | 0 | 64.6 | 0 | 16.2 | Fl |
| 2 | 0 | .049 | 0 | 0 | 0 | 2.1 | 0 | 97.9 | 0 | 8.4 | Fx |
| 3 | 1.7 | 0 | 2.6 | .32 | 2.3 | 45.0 | 7.6 | 43.9 | 1.2 | 12.8 | Fl |
| 4 | 1.0 | .044 | 0 | .24 | 1.3 | 7.9 | 1.2 | 88.8 | 0.7 | 20.3 | Fl |
| 5 | 1.3 | .054 | 0 | 0 | 13.9 | 22.4 | 0.7 | 63.0 | 0 | 2.3 | Fl |
| 6 | 1.1 | .049 | 2.9 | 0 | 4.8 | 58.3 | 2.7 | 33.2 | 0.9 | 42.9 | Fx |
| 7 | 1.1 | .049 | 2.8 | .34 | 4.6 | 54.3 | 1.3 | 39.6 | 0.3 | 36.7 | Fl |

Molar Feed Ratio (HCl:$C_2H_4$:EDC:Air:$N_2$) = 1:1:1:2:1
Temperature = 350° C
*Fx = Fixed Bed Low Surface Area Alumina (e.g. Norton SA 5102) support
Fl = Fluid Bed Low Surface Area Alumina (e.g. Carborundum SAHT 99) support

TABLE II

Effect of Catalyst Composition on Activity

| %Fe | %Rh | %Zn | %Li | T | %$CO_x$ | %VCM | %DCE's | %EDC | %$C_2H_4$ conv. |
|---|---|---|---|---|---|---|---|---|---|
| 1.32 | 0.063 | 3.08 | 0.38 | 350 | 4.0 | 77 | 2.2 | 16.8 | 45.5 |
| 0.02 | 0.069 | 3.43 | 0.35 | 350 | 4.5 | 48.5 | 0.2 | 46.8 | 28.8 |
| 1.39 | 0.029 | 3.04 | 0.37 | 350 | 4.4 | 48.6 | 0.3 | 46.7 | 37.8 |
| 1.44 | 0.069 | 2.16 | 0.35 | 350 | 3.8 | 42.2 | 0.8 | 53.2 | 35.9 |

Fluid Bed
Low Surface Area Alumina Supports
Molar Feed Ratio (HCl:$C_2H_4$:EDC:Air:$N_2$) = 1:1:1:2:1
Temperature = 350° C In examining these tables, particularly Table I, it should be noted that the percentage yield to VCM, carbon oxides, and other chlorohydrocarbons is calculated on the basis of ethylene actually converted. Thus, in the results described in these tables, it is necessary to take into account not only the data with respect to the yield of VCM but also the percentage of ethylene conversion. For example, in the third run described in Table I, 45% of the converted ethylene was VCM, a seemingly acceptable result, however, only 12.8% of the ethylene was converted.

Table I clearly establishes the criticality of iron (or copper), rhodium, and zinc as essential components of the catalyst. In the first five runs described in Table I, one or more of these essential components was omitted, and in most cases the yield of VCM was unacceptably low, and in every case the percentage of ethylene conversion was unacceptably low. The last two runs of Table I were conducted with catalyst compositions within the scope of the present invention, and as to these two runs, it will be noted that both the ethylene conversion and the VCM yield are substantially higher. These two runs also clearly establish that while lithium is a desirable, optional component for the catalyst system (which can substantially extend useful catalyst life) it clearly is not an essential component of the catalyst.

In the second series of experiments, all the essential components of the catalyst system were present, but the concentration of these components was varied. The data in Table II clearly establishes that a catalyst containing at least 0.03% rhodium or platinum, at least 0.02% iron or copper, and at least about 2.2% zinc, that is, a catalyst falling within the scope of the catalyst of the present invention as defined hereinbefore, will provide satisfactory ethylene conversions and VCM yields.

A still further series of experiments was conducted, in which the catalyst composition was maintained constant, and the operating conditions were varied. The data from these experiments are set forth in Table III, which clearly indicates that the catalyst of the present invention can be employed at a variety of temperatures and pressures and in either fixed or fluid bed reactors. Other operating variables, such as contact time (and/or volumetric flow note), and molar feed radio, were, examined in conducting Example 1-10.

In examining the data in Table III, it should be again noted that catalyst composition was not varied, only the operating conditions were varied. In this particular series of tests, the specific catalyst composition employed tended to produce higher VCM yields but lower ethylene conversions and higher oxides, when the temperature and/or pressure were increased. It is to be expected that any given catalyst composition will have a series of optimum operating conditions and/or that for any given series of operating conditions there will be slight differences in the optimum catalyst composition.

TABLE III

Effect of Operating Variables on Activity

| | Variables | | |
|---|---|---|---|
| | Temperature | Pressure | Reactor Design |
| Temperature (° C) | 350 | 400 | 350 | 350 |
| Pressure psig | 0 | 0 | 45 | 0 |
| Reactor Design | Fixed | Fixed | Fixed | Fluid |
| Reaction Products: | | | | |
| %VCM | 56.8 | 69.9 | 43.0 | 55.7 |
| %DCE's | 1.9 | 3.3 | 1.4 | 1.4 |
| %EDC | 36.5 | 17.8 | 46.6 | 37.6 |
| Others | 0 | 1.4 | 0.5 | 0 |
| %C$_2$H$_4$ conv. | 41.3 | 21.6 | 27.1 | 47.8 |
| C$_2$H$_4$ Selectivity: | | | | |
| % Chlorohydrocarbons | 95.2 | 92.4 | 91.5 | 94.7 |
| % Carbon Oxides | 4.8 | 7.6 | 8.5 | 5.3 |

TABLE III-continued

Effect of Operating Variables on Activity

| | Variables | | |
|---|---|---|---|
| | Temperature | Pressure | Reactor Design |
| Catalyst Composition: | Molar Feed Ratio | | |
| %Fe ≈ 1% | (HCl:C$_2$H$_4$:EDC:Air:N$_2$) | | |
| %Rh ≈ 0.05% | = 1:1:1:2:1 | | |
| %Zn ≈ 3% | | | |
| %Li ≈ 0.3% | | | |
| Carrier: | | | |
| Low Surface Area Alumina | | | |

The selection of a particular catalyst composition and operating conditions can also be influenced by extraneous considerations, such as economic conditions. For example, if one has a substantial use for ethylene dichloride, and lacks any other use for the unconverted ethylene, the first run described in Table III would be attractive. On the other hand, if one had a substantial excess of EDC already on hand, and several other processes in which unconverted ethylene might be employed, then the higher temperature, second run of Table III would be desirable.

In other words, from the examples and Tables II and III, it will be clear that by varying catalyst composition and/or operating conditions, it is possible to control not only the conversion of ethylene and co-reactants and the yield of VCM, but also, at least to some degree, the conversion of by-products in the effluent gas from the reactor. It will also be clear that the choice of an optimum catalyst composition and/or an optimum set of operating conditions is a function not only of the novel catalyst and process of the present invention, but also of other factors wholly extraneous to the catalyst and/or the process. In addition, even as to a given starting catalyst composition, the optimum process variable will change as the catalyst composition changes during use, e.g. from evaporation losses.

In commercial OHC reactors, evaporation losses of 10% or more per year are not uncommon, and "make-up catalyst" is added from time to time to replace these losses. It is also to be anticipated, that the use of the catalyst of the present invention in a commercial reactor over a prolonged period would also result in a gradual evaporation loss of iron or copper chloride. The evaporation loss would be expected to vary according to reaction conditions, particularly temperature.

For example, it has been calculated that while only about 0.5% of the cupric chloride would evaporate in a year's use at temperatures of approximately 340°-350° C, at temperatures of 420° C, losses of 3-6% or more could be encountered. For this reason, the catalyst loading and particularly the ratio of rhodium, zinc and lithium chloride to copper or iron chloride in the make-up catalyst may have to be adjusted to a significantly higher iron or copper chloride level, so that when the make-up catalyst is added to the reactor, and admixed with the catalyst already present, the overall atomic ratio of metals in the catalyst in the bed will be adjusted to approximately that of the fresh catalyst salts originally charged to the reactor.

While it is possible to closely approximate metal chloride evaporation losses by calculation based on reaction conditions, it is clearly preferable to adjust the metals ratios in the make-up catalyst by actual quantitative data. This data can be acquired directly from analysis of periodic samplings of the catalyst bed, or indirectly, from any of a number of sources, such as monitoring of the iron or copper content of the aqueous condensate from the reactors, etc.

The ability of the catalyst of the present invention to function effectively at a temperature of 350° C or below is, of course, a significant advantage in substantially reducing the volatility of the catalyst components. Still, further improvement can be obtained, however, by the addition of from about 0.01% to about 3% by weight lithium. Alkaline metal chlorides, particularly potassium chloride, and some alkaline earth metal chlorides, have long been known as having utility as catalyst modifiers to reduce the volatility of oxyhydrochlorination catalysts. Suprisingly, in conjunction with the catalyst of the present invention, only lithium appears to have any utility as a catalyst modifier.

This was clearly established by a series of life study experiments. In the blank or standard test, a catalyst within the scope of the present invention containing 0.05% rhodium, 0.6% iron, and 2.7% zinc was found to have a useful life of approximately 1 month prior to a sharp decline in the yield of VCM and the percentage of ethylene converted, as well as a significant rise in the percentage of carbon oxides. The addition of 0.3% lithium chloride to this catalyst system increased the life of the catalyst substantially.

In similar tests, neither calcium chloride nor rubidium chloride seemed to have any substantial effect on the useful life of the catalyst; while sodium chloride, cesium chloride, barium chloride, and magnesium chloride all significantly reduced the useful life of the catalyst, generally to a period of less than about 1 week. Attempts to substitute potassium chloride for the lithium chloride resulted in a catalyst having unacceptably low activity even when fresh, so that, in essence, this catalyst had no useful life whatever. While sodium is not a suitable substitute for lithium as the modifying metal in the catalyst composition of the present invention, alumina supports having from about 0.2 to about 1.0% sodium oxide do appear to have an optimization advantage.

Again, while optimum results would appear to be achieved employing a catalyst containing rhodium, iron, zinc, and lithium on a low-surface area alumina support containing a small amount of sodium oxide, optimum relates to the percentage of ethylene conversion and the VCM yield. As noted hereinbefore, this may not always be the case, and where there is an alternative use for the unconverted ethylene and a desire to produce additional EDC or other chlorohydrocarbon by-products, the reaction equilibrium can be shifted in that direction either by adjustment of the operating conditions and/or by adjustment of the catalyst composition. In such a case, adjustment of the catalyst composition might also encompass use of substitute materials.

For example, it has already been noted that copper chloride may be substituted for iron chloride. The substitution of iridium, or cerium for rhodium has generally been a less desirable substitution and has generally resulted in a lowering of the percentage of ethylene conversion, a lowering of the VCM selectivity, and a higher concentration of chlorohydrocarbon by-products.

While we decline to accept any one theory by which the functioning of the catalyst or process of the present invention might be explained, it would appear that the iron or copper chloride and possibly the rhodium chloride function as a highly selective oxyhydrochlorination catalyst system, while the zinc chloride probably functions as a dehydrochlorination catalyst promoting the pyrolysis of EDC to VCM.

On the other hand, it is impossible to even speculate as to the specific kinetics of the reaction equilibrium in the reactor; that is to say, how much if any of the VCM is derived from pyrolysis of EDC in the feed stream, as opposed to EDC formed in situ by oxyhydrochlorination of the ethylene in the feed stream. It is clear, however, that the catalyst of the present invention probably produces at least some of the VCM by simultaneous oxyhydrochlorination and pyrolysis. This is clearly established by Example 8, in which the feed stream was composed only of ethylene, oxygen and hydrogen chloride, that is to say where the variation from the preceding examples was the omission of EDC from the feed stream.

What is claimed is:

1. A catalyst for production of VCM comprising from about 0.01 to about 6% by weight of a salt of a metal selected from the group consisting of rhodium and platinum, from about 0.01 to about 15% of a salt of a metal selected from the group consisting of iron and copper, and from about 1.0 to about 25% of a salt of zinc; impregnated on a support selected from the group consisting of alumina, titania, zirconia, silica, and silica alumina; said percentages expressing the metal content of each component as a function of the total weight of the catalyst.

2. The catalyst according to claim 1 wherein said salts are salts of rhodium, iron, and zinc.

3. The catalyst according to claim 1 wherein said catalyst contains from about 0 to about 3% of a salt of lithium.

4. The catalyst according to claim 1 wherein said support is a high purity alumina having a surface area of from about 0.1 to about 10.0 m$^2$/g and containing from about 0.2 to about 1.0% sodium oxide.

5. The catalyst according to claim 1 comprising from about 0.03 to about 2.0% by weight of a salt of rhodium, from about 0.02% to about 10% of a salt of iron, and about 2.2% to about 15% of a salt of zinc.

6. The catalyst according to claim 5 wherein said catalyst contains from about 0 to about 3% of a salt of lithium.

7. The catalyst according to claim 5 wherein said support is a high purity alumina having a surface area of from about 0.1 to about 10.0 m$^2$/g and containing from about 0.2 to about 1.0% sodium oxide.

* * * * *